(12) United States Patent
Ahn et al.

(10) Patent No.: US 11,091,592 B2
(45) Date of Patent: Aug. 17, 2021

(54) POLYMERIZABLE COMPOSITION

(71) Applicant: LG CHEM, LTD., Seoul (KR)

(72) Inventors: Ki Ho Ahn, Daejeon (KR); Sang Woo Kim, Daejeon (KR); Seung Hee Lee, Daejeon (KR); Yulliana Kim, Daejeon (KR)

(73) Assignee: LG CHEM, LTD., Seoul (KR)

(*) Notice: Subject to any disclaimer, the term of this patent is extended or adjusted under 35 U.S.C. 154(b) by 117 days.

(21) Appl. No.: 16/347,031

(22) PCT Filed: Oct. 18, 2017

(86) PCT No.: PCT/KR2017/011515
§ 371 (c)(1),
(2) Date: May 2, 2019

(87) PCT Pub. No.: WO2018/084465
PCT Pub. Date: May 11, 2018

(65) Prior Publication Data
US 2019/0276605 A1 Sep. 12, 2019

(30) Foreign Application Priority Data
Nov. 4, 2016 (KR) .................. 10-2016-0146686

(51) Int. Cl.
C08G 73/02 (2006.01)
C08L 81/02 (2006.01)
(Continued)

(52) U.S. Cl.
CPC ........ C08G 73/0253 (2013.01); C07C 255/54 (2013.01); C07C 323/20 (2013.01);
(Continued)

(58) Field of Classification Search
CPC ........ C08G 65/40; C08G 67/00; C08G 73/00; C08G 33/00
See application file for complete search history.

(56) References Cited

U.S. PATENT DOCUMENTS 8,981,036 B2 3/2015 Keller et al.
2014/0378642 A1* 12/2014 Keller .................. C08G 67/00
528/193
(Continued)

FOREIGN PATENT DOCUMENTS

CN 102976972 A 3/2013
CN 103408755 A 11/2013
(Continued)

OTHER PUBLICATIONS

Ozer, L. M. et al., "Synthesis, Characterization, OFET and Electrochemical Properties of Novel Dimeric Metallophthalocyanines", Dalton Transactions, Feb. 19, 2013, vol. 42, No. 18, pp. 6633-6644.
(Continued)

Primary Examiner — Shane Fang
(74) Attorney, Agent, or Firm — Dentons US LLP

(57) ABSTRACT

The polymerizable composition of the present application may exhibit a wide process window to have excellent workability, and may form a phthalonitrile resin having excellent heat resistance or a prepolymer thereof.

15 Claims, 3 Drawing Sheets

(51) Int. Cl.
| | |
|---|---|
| *C08G 75/0222* | (2016.01) |
| *C08G 73/06* | (2006.01) |
| *C08L 79/04* | (2006.01) |
| *C07C 255/54* | (2006.01) |
| *C08G 75/12* | (2016.01) |
| *C07C 323/20* | (2006.01) |
| *C08K 5/00* | (2006.01) |
| *C08G 75/02* | (2016.01) |

(52) U.S. Cl.
CPC ......... *C08G 73/026* (2013.01); *C08G 73/065* (2013.01); *C08G 73/0644* (2013.01); *C08G 73/0672* (2013.01); *C08G 75/02* (2013.01); *C08G 75/0222* (2013.01); *C08G 75/12* (2013.01); *C08K 5/00* (2013.01); *C08L 79/04* (2013.01); *C08L 81/02* (2013.01)

(56) References Cited

U.S. PATENT DOCUMENTS

| | | |
|---|---|---|
| 2016/0168327 A1 | 6/2016 | Keller et al. |
| 2016/0311976 A1 | 10/2016 | Laskoski et al. |

FOREIGN PATENT DOCUMENTS

| | | |
|---|---|---|
| CN | 107001616 A | 8/2017 |
| KR | 10-2001-0072625 A | 7/2001 |
| KR | 10-0558158 B1 | 3/2006 |
| KR | 10-2016-0059444 A | 5/2016 |
| WO | 99-36446 A1 | 7/1999 |
| WO | 99/36446 A1 | 7/1999 |
| WO | 2016-080762 A1 | 5/2016 |

OTHER PUBLICATIONS

Dafei Zhou et al. "The relationship between processing and performances of polyarylene ether nitriles terminated with ohthalonitrile/trifunction al phthalonitrile composite," Oct. 16, 2012, Journal of Polymer (3 pages).

Yang, et al. "The Relationship between processing and performances of polyarylene ether nitriles terminated with ophthalonitrile/trifuncitional phthalonitrile composites," J Polym Res, Oct. 12, 2015 (9 pages).

* cited by examiner

POLYMERIZABLE COMPOSITION

The present application is a National Phase entry pursuant to 35 U.S.C. 371 of International Application No. PCT/KR2017/011515 filed Oct. 18, 2017, and claims priority to and the benefit of Korean Patent Application No. 10-2016-0146686 filed Nov. 4, 2016, the disclosure of which is incorporated herein by reference in its entirety.

FIELD

The present application relates to a polymerizable composition, a prepolymer, a phthalonitrile resin and a composite.

BACKGROUND

A phthalonitrile resin can be used in various applications. For example, a composite formed by impregnating phthalonitrile resin with a filler such as glass fiber or carbon fiber can be used as a material for automobiles, airplanes, ships, and the like. The process for producing the composite may comprise, for example, mixing a mixture of phthalonitrile and a curing agent, or a prepolymer formed by reaction of the mixture, with the filler and then curing the mixture (see, for example, Patent Document 1).
(Patent Document 1) Korean Patent No. 0558158

SUMMARY

The present application provides a polymerizable composition, a phthalonitrile resin, a composite and a prepolymer.

DETAILED DESCRIPTION

Figure 1:
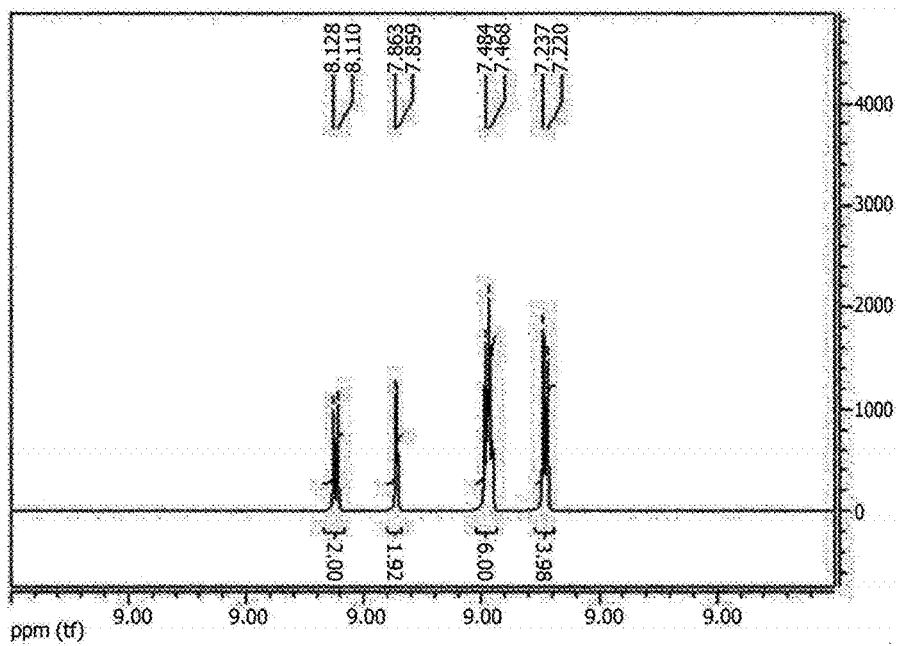
FIGS. 1 to 3 are NMR (nuclear magnetic resonance) analysis results of the compounds prepared in Preparation Examples 1 to 3, respectively.

In the present application, the term alkyl group or alkoxy group may be an alkyl group or alkoxy group having 1 to 20 carbon atoms, 1 to 16 carbon atoms, 1 to 12 carbon atoms, 1 to 8 carbon atoms or 1 to 4 carbon atoms, unless otherwise specified. The alkyl or alkoxy group may be linear, branched or cyclic, which may be optionally substituted with one or more substituents. In the present application, in the range of the term alkyl group, a haloalkyl group may also be included, which is described below.

In the present application, the term alkenyl group or alkynyl group may be an alkenyl group or alkynyl group having 2 to 20 carbon atoms, 2 to 16 carbon atoms, 2 to 12 carbon atoms, 2 to 8 carbon atoms, or 2 to 4 carbon atoms, unless otherwise specified. The alkenyl group or alkynyl group may be linear, branched or cyclic, which may be optionally substituted with one or more substituents.

In the present application, the term aryl group may mean a monovalent residue derived from benzene, a compound containing a benzene structure, or a derivative of any one of the foregoing, unless otherwise specified. The aryl group may comprise, for example, 6 to 25, 6 to 20, 6 to 15 or 6 to 12 carbon atoms. A specific kind of the aryl group may be exemplified by a phenyl group, a benzyl group, a biphenyl group or a naphthalenyl group, and the like, but is not limited thereto. In addition, the category of the aryl group in the present application may include a so-called aralkyl group or arylalkyl group as well as a functional group ordinarily called an aryl group.

In the present application, the term single bond means a case where there is no atom at the relevant site. For example, in a structure of X—Y—Z, when Y is a single bond, X and Z are directly linked to form a structure of X—Z.

In the present application, the term alkylene group or alkylidene group may mean an alkylene group or alkylidene group having 1 to 20 carbon atoms, 1 to 16 carbon atoms, 1 to 12 carbon atoms, 1 to 8 carbon atoms or 1 to 4 carbon atoms, unless otherwise specified. The alkylene group or alkylidene group may be linear, branched or cyclic. In addition, the alkylene group or alkylidene group may be optionally substituted with one or more substituents.

In the present application, the term alkenyl group or alkynylene group may mean an alkenyl group or alkynylene group having 2 to 20 carbon atoms, 2 to 16 carbon atoms, 2 to 12 carbon atoms, 2 to 8 carbon atoms or 2 to 4 carbon atoms, unless otherwise specified. The alkenyl group or alkynylene group may be linear, branched or cyclic. In addition, the alkenyl group or alkynylene group may be optionally substituted with one or more substituents.

In the present application, an example of the substituent which may optionally be substituted in the alkyl group and the like may be exemplified by halogen such as chlorine or fluorine, a haloalkyl group, an epoxy group such as a glycidyl group, a glycidylalkyl group, a glycidoxyalkyl group or an alicyclic epoxy group, an acryloyl group, a methacryloyl group, an isocyanate group, a thiol group, an alkyl group, an alkoxy group or an aryl group, and the like, but is not limited thereto.

The present application relates to a polymerizable composition. The polymerizable composition of the present application comprises a first monomer comprising two functional groups derived from phthalonitrile.

A first monomer of the present application comprises two functional groups derived from phthalonitrile. The functional group derived from phthalonitrile may mean a substituent represented by Formula 4 to be described below. As the first monomer comprises two functional groups derived from phthalonitrile, workability of the polymerizable composition can be improved.

A first monomer of the present application may have a molecular weight of 250 to 3000 or 300 to 2,500. As the molecular weight of the first monomer falls within the above-described range, the polymerizable composition comprising the first monomer may exhibit a low melting temperature and a wide process window, thereby improving the workability of the polymerizable composition.

A first monomer of the present application may be a compound of Formula 1 below.

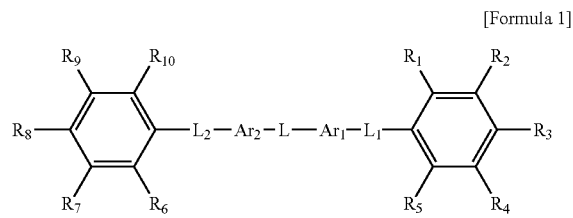

[Formula 1]

In Formula 1, $Ar_1$ and $Ar_2$ are each independently an aromatic divalent radical, L, $L_1$ and $L_2$ are each independently a single bond, an alkylene group, an alkylidene group, an oxygen atom or a sulfur atom, and $R_1$ to $R_{10}$ are each independently hydrogen, an alkyl group, an alkoxy group, an aryl group or a cyano group, provided that at least two of $R_1$ to $R_5$ are each a cyano group and at least two of $R_6$ to $R_{10}$ are each a cyano group.

Here, $Ar_1$ and $Ar_2$ may be the same or different from each other, and L, $L_1$ and $L_2$ may also be the same or different from one another.

In the present application, the term aromatic divalent radical may mean a divalent residue derived from benzene, a compound comprising benzene or a derivative of any one of the foregoing, unless otherwise specified. Here, the compound comprising benzene may mean a compound having a structure in which two or more benzene rings are condensed while sharing two carbon atoms or are linked by an appropriate linker. The aromatic divalent radical may comprise, for example, 6 to 25, 6 to 20, 6 to 15 or 6 to 12 carbon atoms.

In one example, the aromatic divalent radical may be a radical derived from an aromatic compound of Formula 2 below.

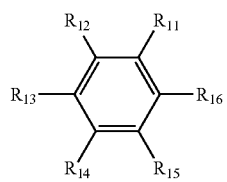

[Formula 2]

In Formula 2, $R_{11}$ to $R_{16}$ are each independently hydrogen, an alkyl group, an alkoxy group or an aryl group, provided that at least two of $R_{11}$ to $R_{16}$ each form a radical.

Here, the formation of a radical may mean that the site is connected to another element of Formula 1. For example, in the case of $Ar_1$ in Formula 1, any one of the radical-forming sites may be directly linked to $L_1$ in Formula 1 to form a covalent bond and the other site may be directly connected to L in Formula 1 to for a covalent bond. In the case of $Ar_2$ in Formula 1, any one of the radical-forming sites may be directly linked to $L_2$ in Formula 1 to form a covalent bond, and the other site may be directly connected to L in Formula 1 to form a covalent bond. Each of the substituents forming no radical may be hydrogen, an alkyl group or an alkoxy group; or hydrogen or an alkyl group. In one example, $R_{11}$ and $R_{14}$ or $R_{11}$ and $R_{13}$ in Formula 2 may form the radical. In this case, the substituents forming no radical may be each independently hydrogen, an alkyl group, an alkoxy group or an aryl group; hydrogen, an alkyl group or an alkoxy group; or hydrogen or an alkyl group.

In Formula 1, L, $L_1$, and $L_2$ may be a single bond, an alkylene group, an alkylidene group, an oxygen atom, or a sulfur atom.

In one example, L in Formula 1 may be a single bond, an alkylene group or an alkylidene group, or may be a sulfur atom. Here, the alkylene group or alkylidene group may be optionally substituted with at least one halogen atom or haloalkyl group, that is, at least one alkyl group substituted with a halogen atom, and in some cases, may also be optionally substituted with other substituents other than a halogen atom have. On the other hand, the term single bond is a case where no atom exists in the relevant site, and for example, when L is a single bond, a structure in which $Ar_1$ and $Ar_2$ are directly connected can be derived.

In Formula 1, $L_1$ and $L_2$ may be each an alkylene group, an alkylidene group or an oxygen atom, and in one example, they may be each an oxygen atom.

In Formula 1, $R_1$ to $R_{10}$ are each independently hydrogen, an alkyl group, an alkoxy group, an aryl group or a cyano group, provided that at least two of $R_1$ to $R_5$ are each a cyano group and at least two of $R_6$ to $R_{10}$ are each a cyano group. In another example, $R_1$ to $R_{10}$ other than a cyano group may be each independently hydrogen, an alkyl group or an alkoxy group; or hydrogen or an alkyl group. In one example, any two of $R_2$ to $R_4$ and any two of $R_7$ to $R_9$ in Formula 1 are each a cyano group, and the remaining substituents are each independently hydrogen, an alkyl group, an alkoxy group or an aryl group; hydrogen, an alkyl group or an alkoxy group; or hydrogen or an alkyl group.

A compound of Formula 1 can be effectively used in various applications where the so-called phthalonitrile compounds are known to be applicable. For example, the phthalonitrile compound can be effectively used as a raw material or a precursor capable of producing a so-called phthalonitrile resin. The compound exhibits a low melting temperature, has excellent reactivity with a curing agent and exhibits a wide process window, whereby it can be effectively applied to the application. The compound may be used as a precursor of a dye such as a phthalocyanine dye, or a precursor or raw material of a fluorescent brightener, a photographic sensitizer or an acid anhydride, in addition to the above-mentioned applications.

A compound of Formula 1 can be synthesized according to known synthesis methods of organic compounds. For example, the compound of Formula 1 can be synthesized by a method of reacting an aromatic compound having a phenolic hydroxy group with an aromatic compound having at least two cyano groups (ex. nitro displacement method), and the like. In the field of organic chemistry, the aromatic compounds capable of forming the structure of the compound of Formula 1 are known, and these compounds can be applied to produce the compounds in consideration of the desired structure.

The polymerizable composition of the present application comprises a second monomer containing three or more functional groups derived from phthalonitrile.

The second monomer of the present application comprises three or more functional groups derived from phthalonitrile. The functional group derived from phthalonitrile of the present application may be a substituent represented by Formula 4 to be described below. The second monomer of the present application may preferably comprise three or more, four or more, five or more, or six or more functional groups derived from phthalonitrile. The upper limit of the functional groups derived from phthalonitrile contained in the second monomer may be 9 or less, 8 or less, or 7 or less. As the second monomer of the present application comprises satisfactorily the functional group derived from phthalonitrile in the above-described range, the polymerizable composition can form a phthalonitrile resin having excellent heat resistance.

The second monomer of the present application may have a molecular weight of 600 to 5,000, or 800 to 4,000. The molecular weight of the second monomer falls within the above-described range, so that the polymerizable composition comprising the second monomer can form a phthalonitrile resin having excellent heat resistance.

The second monomer of the present application may be a compound of Formula 3 below.

$$Ar_3\text{-}L_3\text{-}Ar_4\text{-}L_4\text{-}Ar_5\text{-}L_5\text{-}Ar_6 \qquad \text{[Formula 3]}$$

In Formula 3, $Ar_3$ and $Ar_6$ are the same or different aryl groups from each other, $Ar_4$ and $Ar_5$ are the same or different arylene groups from each other, $L_3$ to $L_5$ are each independently an alkylene group, an alkylidene group, an alkenylene group or an alkynylene group, where $Ar_3$ to $Ar_6$ are each substituted with at least one substituent represented by Formula 4 below.

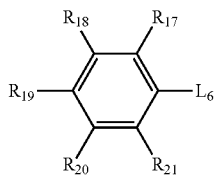

[Formula 4]

In Formula 4, $L_6$ is an alkylene group, an alkylidene group, an oxygen atom or a sulfur atom, and $R_{17}$ to $R_{21}$ are each independently hydrogen, an alkyl group, an alkoxy group, an aryl group or a cyano group, provided that at least two of $R_{17}$ to $R_{21}$ are each a cyano group.

In a compound of Formula 3, $L_3$ to $L_5$ may be each independently an alkylene group or an alkylidene group, having 1 to 4 carbon atoms, and may be, for example, a methylene group or an ethylene group.

In a compound of Formula 3, $Ar_3$ to $Ar_6$ are each an aryl group or an arylene group as described above, where each of these may be substituted with at least one or more substituents of Formula 2 above.

In addition to the substituent of Formula 4, other substituents may be present in $Ar_3$ to $Ar_6$, and an example thereof includes halogen, an epoxy group such as a glycidyl group, an epoxy alkyl group, a glycidoxyalkyl group or an alicyclic epoxy group, an acryloyl group, a methacryloyl group, an isocyanate group, a thiol group, an alkyl group, an alkoxy group or an aryl group, and the like, as described above, and in a suitable example, the alkyl group may be substituted.

That is, each of $Ar_3$ to $Ar_6$ may be substituted with the substituent of Formula 4 and an alkyl group by at least one.

In Formula 3, $Ar_4$ and $Ar_5$ may be an arylene group having 6 to 25, 6 to 20, 6 to 15 or 6 to 12 carbon atoms, and may be, for example, a phenylene group.

When $Ar_4$ and $Ar_5$ are each a phenylene group, the positions of $L_3$ to $L_5$ connected to both of them are not particularly limited. For example, in the case of $Ar_4$, $L_3$ may be bonded to an ortho, meta, or para position based on the position bonded to $L_4$. Also, in the case of $Ar_5$, $L_5$ may be bonded to an ortho, meta, or para position based on the position bonded to $L_4$.

In one example, in the case of $Ar_4$, $L_3$ may be bonded to a meta position based on the position bonded to $L_4$. Also, in the case of $Ar_5$, $L_5$ may be bonded to a meta position based on the position bonded to $L_4$. Such a structure can facilitate maintaining a suitable processing temperature and a wide process window in the process of preparing the phthalonitrile resin.

When $Ar_4$ and $Ar_5$ are each a phenylene group, the position of the substituent of Formula 4 with which each is substituted may be adjusted. For example, in the case of $Ar_4$, the substituent of Formula 2 may be substituted at an ortho, meta or para position based on the position bonded to $L_4$. Also, in the case of $Ar_5$, the substituent of Formula 2 may be substituted at an ortho, meta or para position based on the position bonded to $L_4$.

In one example, in the case of $Ar_4$, the substituent of Formula 4 may be bonded to a para position based on the position bonded to $L_4$. Also, in the case of $Ar_5$, the substituent of Formula 2 may be bonded to a para position based on the position bonded to $L_4$. Such a structure can facilitate maintaining a suitable processing temperature and a wide process window in the process of preparing the phthalonitrile resin.

Other substituents may be present in $Ar_4$ and $Ar_5$ which are each a phenylene group and an example thereof can be exemplified by an alkyl group, specifically, an alkyl group having 1 to 4 carbon atoms, or a methyl group or an ethyl group. For example, in the case of $Ar_4$, the alkyl group may be substituted at an ortho, meta, or para position based on the position bonded to $L_4$. Also, in the case of $Ar_5$, the alkyl group may be substituted at an ortho, meta, or para position based on the position bonded to $L_4$.

In one example, in the case of $Ar_4$, the alkyl group may be substituted at a meta position based on the position bonded to $L_4$. Also, in the case of $Ar_5$, the alkyl group may be substituted at a meta position based on the position bonded to $L_4$. Such a structure can facilitate maintaining a suitable processing temperature and a wide process window in the process of preparing the phthalonitrile resin.

In one example, when $Ar_4$ is phenylene, if the carbon atom bonded to $L_4$ is numbered 1 and the carbon atoms are numbered clockwise, the compound may have a structure that the alkyl group is substituted at the 3-carbon atom, the substituent of Formula 2 is substituted at the 4-carbon atom and the 5-carbon atom is bonded to the $L_3$.

In one example, when $Ar_5$ is phenylene, if the carbon atom bonded to $L_4$ is numbered 1 and the carbon atoms are numbered clockwise, the compound may have a structure that the alkyl group is substituted at the 5-carbon atom, the substituent of Formula 2 is substituted at the 4-carbon atom and the 3-carbon atom is bonded to the $L_5$. Such a structure can facilitate maintaining a suitable processing temperature and a wide process window in the process of preparing the phthalonitrile resin.

In Formula 3, $Ar_3$ and $Ar_6$ may be each an aryl group having 6 to 25, 6 to 20, 6 to 15 or 6 to 12 carbon atoms, and may be, for example, a phenyl group.

When $Ar_3$ and $Ar_6$ are each a phenyl group, the position of the substituent of Formula 4 with which each is substituted may be adjusted. For example, in the case of $Ar_3$, the substituent of Formula 4 may be substituted at an ortho, meta, or para position based on the position bonded to $L_3$. In the case of $Ar_6$, the substituent of Formula 4 may be substituted at an ortho, meta, or para position based on the position bonded to $L_5$.

In one example, in the case of $Ar_3$, the substituent of Formula 4 may be bonded to an ortho position based on the position bonded to $L_3$. In the case of $Ar_6$, the substituent of Formula 4 may be bonded to an ortho position based on the position bonded to $L_5$. Such a structure can facilitate maintaining a suitable processing temperature and a wide process window in the process of preparing the phthalonitrile resin.

Other substituents may be present in $Ar_3$ and $Ar_6$ which are each a phenylene group and an example thereof can be exemplified by an alkyl group, specifically, an alkyl group having 1 to 4 carbon atoms, or a methyl group or an ethyl group. For example, in the case of $Ar_3$, the alkyl group may be substituted at an ortho, meta, or para position based on the position bonded to $L_3$. Also, in the case of $Ar_6$, the alkyl group may be substituted at an ortho, meta, or para position based on the position bonded to $L_5$.

In one example, in the case of $Ar_3$, the alkyl group may be substituted at a meta position based on the position bonded to $L_3$. Also, in the case of $Ar_6$, the alkyl group may be substituted at a meta position based on the position bonded to $L_1$. Such a structure can facilitate maintaining a suitable processing temperature and a wide process window in the process of preparing the phthalonitrile resin.

In one example, when $Ar_3$ is a phenyl group, if the carbon atoms bonded to $L_3$ is numbered 1 and the carbon atoms are numbered clockwise, the compound may have a structure that the alkyl group is substituted at the 3-carbon atom and the substituent of Formula 4 is substituted at the 6-carbon atom.

In one example, when $Ar_6$ is phenylene, if the carbon atoms bonded to $L_5$ is numbered 1 and the carbon atoms are numbered clockwise, the compound may have a structure that the alkyl group is substituted at the 5-carbon atom and the substituent of Formula 2 is substituted at the 2-carbon atom.

Such a structure may be advantageous to maintain a suitable processing temperature and a wide process window in the process of preparing the phthalonitrile resin.

In Formula 4, $L_6$ may be an alkylene group, an alkylidene group, an oxygen atom or a sulfur atom, and may be, for example, an oxygen atom.

A polymerizable composition of the present application can determine a content ratio of the first monomer and the second monomer in consideration of the physical properties of the phthalonitrile resin formed from the polymerizable composition. In one example, the polymerizable composition of the present application may comprise 5 mol to 150 mol or 30 mol to 120 mol of the second monomer relative to 100 mol of the first monomer. In one example, the polymerizable composition of the present application may comprise 5 to 250 parts by weight or 60 to 220 parts by weight of the second monomer relative to 100 parts by weight of the first monomer. By controlling the ratio of blending the first monomer having relatively good workability but relatively low heat resistance and the second monomer having relatively good heat resistance but relatively poor workability, the polymerizable composition may have not only a wide process window, but also the polymerizable composition may form a phthalonitrile resin having excellent heat resistance.

In a second monomer of the present application, a homopolymer formed from the second monomer may have a glass transition temperature ($T_g$) higher than a glass transition temperature ($T_g$) of the homopolymer formed from the first monomer. The polymerizable composition of the present application can form a phthalonitrile resin having excellent heat resistance and have a wide process window by blending the second monomer having excellent heat resistance to the first monomer having a relatively low heat resistance.

In the second monomer of the present application, the homopolymer formed from the second monomer may have a melting temperature ($T_m$) higher than a melting temperature ($T_m$) of the homopolymer formed from the first monomer. The polymerizable composition of the present application can form a phthalonitrile resin having excellent heat resistance and have a wide process window by blending the second monomer having excellent heat resistance to the first monomer having a relatively low heat resistance.

In the first monomer of the present application, the homopolymer formed from the first monomer may have a glass transition temperature ($T_g$) of 30° C. to 300° C. In one example, in the first monomer, the homopolymer formed from the first monomer may have a glass transition temperature ($T_g$) of 300° C. or lower, 250° C. or lower, or 200° C. or lower. In another example, in the first monomer, the homopolymer formed from the first monomer may have a glass transition temperature ($T_g$) of 30° C. or higher, 40° C. or higher, or 50° C. or higher. By using the first monomer in which the upper limit and the lower limit of the glass transition temperature in the homopolymer formed from the first monomer satisfy the above range, it is possible to provide a polymerizable composition having a wide process window and thus excellent workability.

In the first monomer of the present application, the homopolymer formed from the first monomer may have a melting temperature ($T_m$) of 30° C. to 300° C. In one example, in the first monomer, the homopolymer formed from the first monomer may have a melting temperature ($T_m$) of 300° C. or lower, 250° C. or lower, or 200° C. or lower. In another example, in the first monomer, the homopolymer formed from the first monomer may have a melting temperature ($T_m$) of 30° C. or higher, 40° C. or higher, or 50° C. or higher. By using the first monomer in which the upper limit and the lower limit of the melting temperature in the homopolymer formed from the first monomer satisfy the above range, it is possible to provide a polymerizable composition having a wide process window and thus excellent workability.

In the second monomer of the present application, the homopolymer formed from the second monomer may have a glass transition temperature ($T_g$) of 50° C. to 300° C. In one example, in the second monomer, the homopolymer formed from the second monomer may have a glass transition temperature ($T_g$) of 50° C. or higher, 70° C. or higher, or 80° C. or higher. In another example, in the second monomer, the homopolymer formed from the second monomer may have a glass transition temperature ($T_g$) of 300° C. or lower, 280° C. or lower, or 250° C. or lower. It is possible to provide a polymerizable composition capable of forming a phthalonitrile resin having excellent heat resistance by using the second monomer in which the upper limit and the lower limit of the glass transition temperature in the homopolymer formed from the second monomer satisfy the above range.

In the second monomer of the present application, the homopolymer formed from the second monomer may have a melting temperature ($T_m$) of 50° C. to 300° C. In one example, in the second monomer, the homopolymer formed from the second monomer may have a melting temperature ($T_m$) of 50° C. or higher, 70° C. or higher, or 80° C. or higher. In another example, in the second monomer, the homopolymer formed from the second monomer may have a melting temperature ($T_m$) of 300° C. or lower, 280° C. or lower, or 250° C. or lower. It is possible to provide a polymerizable composition capable of forming a phthalonitrile resin having excellent heat resistance by using the first monomer in which the upper limit and the lower limit of the melting temperature in the homopolymer formed from the second monomer satisfy the above range.

A polymerizable composition of the present application may further comprise a curing agent. The type of the usable curing agent is not particularly limited as long as it is capable of reacting with the first monomer and the second monomer of the present application to form a polymer, and for example, any compound known to be useful for formation of a phthalonitrile resin can also be used.

In one example, an amine compound such as an aromatic amine compound or a hydroxy compound can be used as a curing agent. In the present application, the hydroxy compound may mean a compound containing at least one or two hydroxy groups in the molecule.

In one example, as a curing agent, a compound represented by Formula 5 may be used. The curing agent of Formula 5 has an imide structure in the molecular structure, thereby exhibiting excellent heat resistance, so that it can form a polymerizable composition not generating voids or the like that can adversely affect physical properties, even when it is contained in an excess amount in the polymerizable composition or the polymerizable composition is processed or cured at a high temperature.

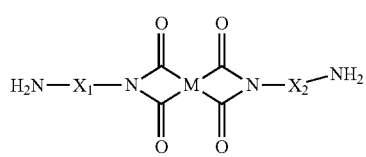

[Formula 5]

In Formula 5, M is a tetravalent radical, and $X_1$ and $X_2$ are each independently an alkylene group, an alkylidene group or an aromatic divalent radical.

In the present application, the term n-valent radical (where n is an arbitrary number) may mean an n-valent residue derived from a predetermined compound, unless otherwise specified. For example, in Formula 5, M may be a tetravalent radical derived from an aliphatic, alicyclic or aromatic compound, and in this case, for example, M may have a structure in which radials formed by eliminating four hydrogen atoms from the aliphatic, alicyclic or aromatic compound are connected to carbon atoms of carbonyl groups in Formula 5, respectively.

Here, an aliphatic compound can be exemplified by a linear or branched alkane, alkene or alkyne. As the aliphatic compound, alkane, alkene or alkyne having 2 to 20 carbon atoms, 2 to 16 carbon atoms, 2 to 12 carbon atoms, 2 to 8 carbon atoms or 2 to 4 carbon atoms may be used. In this case, the alkane, alkene or alkyne may optionally be substituted with one or more substituents.

Here, an alicyclic compound can be exemplified by a hydrocarbon compound comprising a non-aromatic ring structure having 3 to 20 carbon atoms, 3 to 16 carbon atoms, 3 to 12 carbon atoms, 3 to 8 carbon atoms or 3 to 4 carbon atoms. Such an alicyclic hydrocarbon compound may contain at least one heteroatom such as oxygen or nitrogen as a ring constituting atom and may optionally be substituted with one or more substituents, if necessary.

In addition, the aromatic compound can be exemplified by benzene, a compound comprising benzene or a derivative of any one of the foregoing. Here, the compound comprising benzene may mean a compound having a structure in which two or more benzene rings are condensed while sharing one or two carbon atoms, or directly linked, or a structure in which they are linked by an appropriate linker. The aromatic compound may comprise, for example, 6 to 25, 6 to 20 or 6 to 12 carbon atoms and may be optionally substituted with one or more substituents.

In one example, the alicyclic or aromatic compound forming the tetravalent radical can be exemplified by a compound represented by any one of Formulas 6 to 11 below.

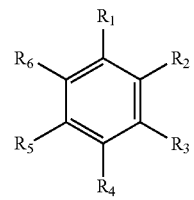

[Formula 6]

In Formula 6, $R^1$ to $R^6$ are each independently hydrogen, an alkyl group, an alkoxy group or an aryl group.

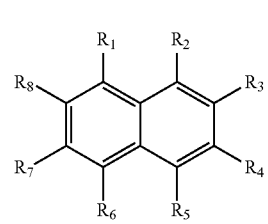

[Formula 7]

In Formula 7, $R^1$ to $R^8$ are each independently hydrogen, an alkyl group, an alkoxy group or an aryl group.

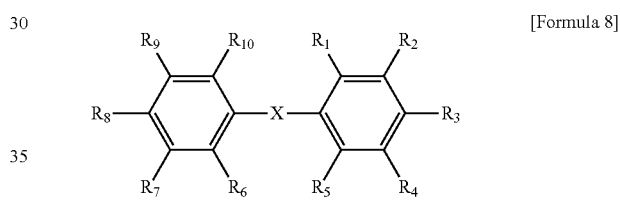

[Formula 8]

In Formula 8, $R^1$ to $R^{10}$ are each independently hydrogen, an alkyl group, an alkoxy group or an aryl group, and X is a single bond, an alkylene group, an alkylidene group, an oxygen atom, a sulfur atom, a carbonyl group, -$A^1$-O-C(=O)-$A^2$-, -$A^1$-C(=O)-O-$A^2$-, -S(=O)- or -S(=O)$_2$-. Here, $A^1$ and $A^2$ may be each independently a single bond or an alkylene group.

In this specification, the term single bond means a case where no separate atom exists in the relevant site, and for example, when X in Formula 8 is a single bond, it means a case where no separate atom exists in the relevant site, where the benzene rings on both sides of X may be directly connected to form a biphenyl structure.

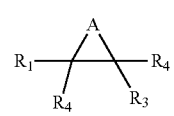

[Formula 9]

In Formula 9, $R^1$ to $R^4$ are each independently hydrogen, an alkyl group or an alkoxy group, and A is an alkylene group or an alkenylene group.

In Formula 9, two of $R^1$ to $R^4$ may also be connected to each other to form an alkylene group, and the alkylene group or alkenylene group of A may contain one or more oxygen atoms as the heteroatom.

[Formula 10]

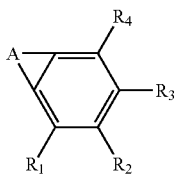

In Formula 10, $R^1$ to $R^4$ are each independently hydrogen, an alkyl group or an alkoxy group, and A is an alkylene group.

[Formula 11]

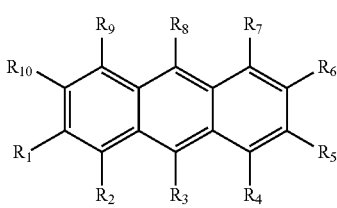

In Formula 11, $R^1$ to $R^{10}$ are each independently hydrogen, an alkyl group or an alkoxy group.

In the present application, the term alkyl group may be an alkyl group having 1 to 20 carbon atoms, 1 to 16 carbon atoms, 1 to 12 carbon atoms, 1 to 8 carbon atoms or 1 to 4 carbon atoms, unless otherwise specified. The alkyl group may be linear, branched or cyclic and, if necessary, may be substituted with one or more substituents.

In the present application, the term alkoxy group may be an alkoxy group having 1 to 20 carbon atoms, 1 to 16 carbon atoms, 1 to 12 carbon atoms, 1 to 8 carbon atoms or 1 to 4 carbon atoms, unless otherwise specified. The alkoxy group may be linear, branched or cyclic and, if necessary, may be substituted with one or more substituents.

In the present application, the term aryl group may mean a monovalent residue derived from the above-described aromatic compound, unless otherwise specified. In the present application, the category of the term aryl group may include not only a functional group commonly referred to as an aryl group but also an aralkyl group or an arylalkyl group, and the like.

In the present application, the term alkylene group or alkylidene group may mean an alkylene group or alkylidene group having 1 to 20 carbon atoms, 1 to 16 carbon atoms, 1 to 12 carbon atoms, 1 to 8 carbon atoms or 1 to 4 carbon atoms, unless otherwise specified. The alkylene group or alkylidene group may be linear, branched or cyclic. In addition, the alkylene group or alkylidene group may be optionally substituted with one or more substituents.

In the present application, the substituent with which the aliphatic compound, the alicyclic compound, the aromatic compound, the alkyl group, the alkoxy group, the aryl group, the alkylene group or the alkylidene group, and the like may be optionally substituted may be exemplified by halogen such as chlorine or fluorine, an epoxy group such as a glycidyl group, an epoxyalkyl group, a glycidoxyalkyl group or an alicyclic epoxy group, an acryloyl group, a methacryloyl group, an isocyanate group, a thiol group, an alkyl group, an alkoxy group or an aryl group, and the like, but is not limited thereto.

Here, the compound of Formula 6 can be exemplified by benzene, alkylbenzene or dialkylbenzene, and the like, but is not limited thereto.

In addition, the compound of Formula 8 can be exemplified by biphenyl or a compound represented by any one of Formulas A to F below, but is not limited thereto.

[Formula A]

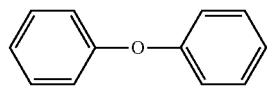

[Formula B]

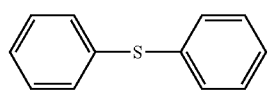

[Formula C]

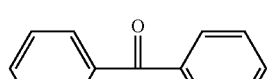

[Formula D]

[Formula E]

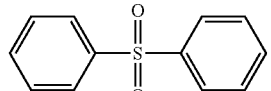

[Formula F]

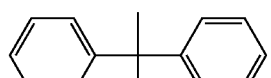

Here, a compound of Formula 9 can be exemplified by, for example, a cycloalkane having 4 to 8 carbon atoms such as cyclohexane, cyclohexene which may be substituted with at least one alkyl group, and the like, or a compound represented by any one of Formulas G to I, but is not limited thereto.

[Formula G]

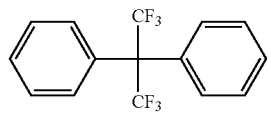

[Formula H]

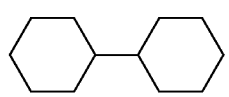

[Formula I]

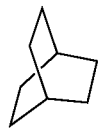

Here, a compound of Formula 10 can be exemplified by a compound represented by Formula J below which may be substituted with at least one alkyl group, but is not limited thereto.

[Formula J]

In the compound as above, for example, four hydrogen atoms may be eliminated to form radicals, and the radicals may be included in the structure of Formula 5.

These radicals may be formed by directly eliminating $R^1$ to $R^{10}$ which are substituents of Formulas 6 to 11, or may also be formed by eliminating hydrogen atoms belonging to the alkyl group, alkoxy group, aryl group, alkylene group or alkenylene group, which is a substituent that may exist in $R^1$ to $R^{10}$.

For example, when the radicals are derived from the compound of Formula 6, one or more, two or more, three or more, or four of $R^1$ to $R^6$ of Formula 6 may form the radicals, or the radicals may be formed by eliminating hydrogen atoms of the alkyl group, alkoxy group or aryl group present in $R^1$ to $R^6$. Here, the formation of a radical may mean that the site is linked to the carbon atom of the carbonyl group of Formula 5, as described above. For example, when $R^2$, $R^3$, $R^5$ and $R^6$ in Formula 6 form radicals connected to Formula 5, the same core structure as the compound CA1 to be described below can be formed.

In one example, the tetravalent radical of Formula 5 may be a tetravalent radical derived from a compound represented by any one of Formulas 6 to 8. In this case, $R^1$ to $R^6$ in Formula 6, $R^1$ to $R^8$ in Formula 7 or $R^1$ to $R^{11}$ in Formula 8 are each independently hydrogen, an alkyl group, an alkoxy group or an aryl group, but four or more of the above substitutents may form radicals connected to Formula 5. Each of which forms no radical may be hydrogen, an alkyl group or an alkoxy group, or may be hydrogen or an alkyl group. In one example, $R^2$, $R^3$, $R^5$ and $R^6$ in Formula 6 may form the radicals, and $R^1$ and $R^4$ may be each independently hydrogen, an alkyl group, an alkoxy group or an aryl group, or may be a hydrogen, an alkyl group or an alkoxy group, or may be hydrogen or an alkyl group. Also, in Formula 7, $R^3$, $R^4$, $R^8$ and $R^7$ may form the radicals, and $R^1$, $R^2$, $R^5$ and $R^6$ may be each independently hydrogen, an alkyl group, an alkoxy group or an aryl group, or may be hydrogen, an alkyl group or an alkoxy group, or may be hydrogen or an alkyl group. Furthermore, in Formula 8, $R^2$, $R^3$, $R^8$ and $R^9$ may form the radicals, and $R^1$, $R^4$, $R^5$, $R^6$, $R^7$ and $R^{10}$ may be each independently hydrogen, an alkyl group, an alkoxy group or an aryl group, or may be hydrogen, an alkyl group or an alkoxy group, or may be hydrogen or an alkyl group.

In Formula 8, X may be an alkylene group, an alkylidene group, an oxygen atom or a sulfur atom. In another example, X in Formula 8 may be an alkylene group, an alkylidene group, an oxygen atom or an oxygen atom.

In Formula 5, $X^1$ and $X^2$ may be each independently an alkylene group, an alkylidene group or an aromatic divalent radical, and in another example, they may be the same or different aromatic divalent radicals. Here, the aromatic divalent radical may be a divalent radical derived from the above-mentioned aromatic compound.

In one example, $X^1$ and $X^2$ in Formula 5 may be each independently a divalent radical derived from a compound represented by any one of Formulas 12 to 14 below.

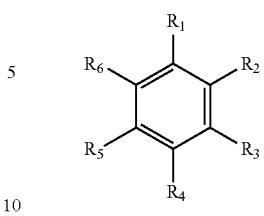

[Formula 12]

In Formula 12, $R^1$ to $R^6$ are each independently hydrogen, an alkyl group, an alkoxy group, an aryl group, a hydroxy group or a carboxyl group.

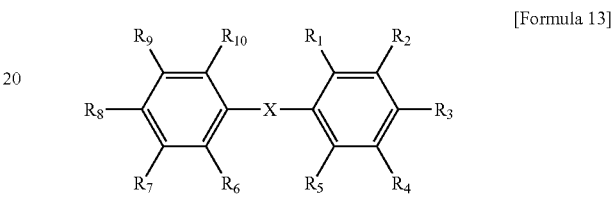

[Formula 13]

In Formula 13, $R^1$ to $R^{10}$ are each independently hydrogen, an alkyl group, an alkoxy group, a hydroxy group, a carboxyl group or an aryl group, and X is a single bond, an alkylene group, an alkylidene group, an oxygen atom, a sulfur atom, a carbonyl group, —$NR^{11}$—, —$S(=O)$— or —$S(=O)^2$—, where $R^{11}$ is hydrogen, an alkyl group, an alkoxy group or an aryl group.

Here, the meaning of the single bond is as defined in Formula 4.

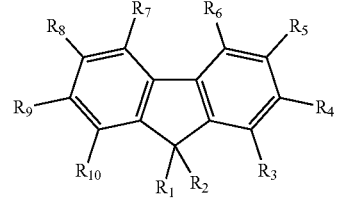

[Formula 14]

In Formula 14, $R^1$ to $R^{10}$ are each independently hydrogen, an alkyl group, an alkoxy group, a hydroxy group, a carboxyl group or an aryl group.

A compound of Formula 12 can be exemplified by benzene which may be substituted with at least one hydroxy group or carboxyl group, but is not limited thereto.

A compound of Formula 13 can be exemplified by biphenyl which may be substituted with at least one hydroxy group or carboxyl group, a compound represented by any one of Formulas A to F above, a compound which is represented by any one of Formulas A to F above and simultaneously may be substituted with at least one hydroxy group or carboxyl group, a compound represented by Formulas K to N below, or a compound which is represented by Formulas K to N below and simultaneously may be substituted with at least one hydroxy group or carboxyl group, but is not limited thereto.

[Formula K]

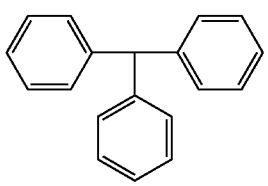

[Formula L]

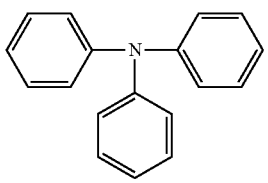

[Formula M]

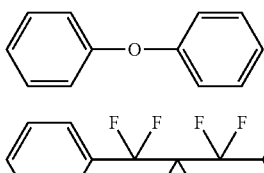

[Formula N]

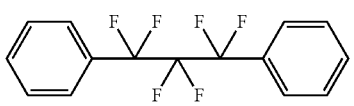

A compound of Formula 14 can be exemplified by a compound represented by Formula O below or a compound which is represented by Formula O above and simultaneously may be substituted with at least one hydroxy group or carboxyl group, but is not limited thereto.

[Formula O]

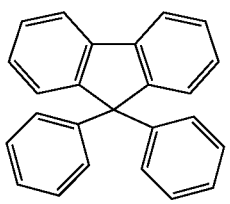

In one example, the aromatic divalent radical may be a radical derived from the compound of Formula 12 above, the example of which may include phenylene, but is not limited thereto. When the divalent radical is phenylene, the substitution position of the amine group based on the site connected to N in $X^1$ of Formula 5 may be an ortho, meta or para position, and the substitution position of the amine group based on the site connected to N in $X^2$ of Formula 5 may also be an ortho, meta or para position.

A compound of Formula 5 can be synthesized according to known synthesis methods of organic compounds, and the specific method thereof is not particularly limited. For example, the compound of Formula 5 can be formed by a dehydration condensation reaction of a dianhydride compound and a diamine compound or the like.

The compound of Formula 5 has a high boiling point and thus is not volatilized or decomposed at a high temperature, whereby hardenability of the polymerizable composition is stably maintained and simultaneously voids are not generated, which can adversely affect physical properties of a composite during processing at a high temperature or curing. Accordingly, in one example, the compound may have a decomposition temperature of 300° C. or higher, 350° C. or higher, 400° C. or higher, or 500° C. or higher. In the present application, the term decomposition temperature may mean a temperature at which the decomposition rate of the compound of Formula 5 is maintained in a range of 10% or less, 5% or less, or 1% or less. Here, the upper limit of the decomposition temperature is not particularly limited and may be, for example, about 1,000° C. or less.

Furthermore, the compound of Formula 5 can easily adjust reactivity or a process window of the polymerizable composition itself, that is, a difference between a melting temperature and a curing temperature of the polymerizable composition or a prepolymer formed therefrom by selection of M of the core or $X^1$ or $X^2$ of a linker to function as a curing agent having various physical properties depending on the application.

In one example, as the curing agent, a compound of Formula 15 below may be used.

[Formula 15]

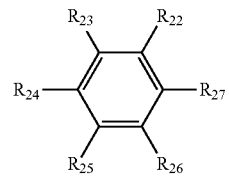

In Formula 15, $R_{22}$ to $R_{27}$ are each independently hydrogen, an alkyl group, an alkoxy group, an aryl group, an amine group or a substituent group of Formula 16 below, provided that two or more of $R_{22}$ to $R_{27}$ are each an amine group or a substituent of Formula 16 below.

[Formula 16]

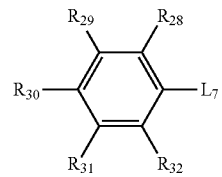

In Formula 16, $L_7$ is an alkylene group, an alkylidene group, an oxygen atom or a sulfur atom, and $R_{28}$ to $R_{32}$ are each hydrogen, an alkyl group, an alkoxy group, an aryl group or amine group, provided that at least one of $R_{28}$ to $R_{32}$ is an amine group.

When the substituent of Formula 16 is present, $L_7$ in the above structure may be linked to the benzene ring of Formula 15.

In one example, the curing agent may be a compound in which two of $R_{22}$ to $R_{27}$ in Formula 15 are each the substituent of Formula 16. In this case, in Formula 15, the two substituents of Formula 16 may have a structure in which based on any one of them, the other one is present at an otho, meta or para position, where it may be present, particularly, at a meta position. Also, in this case, any one of $R_{28}$ to $R_{32}$ in the substituent of Formula 16 may be an amine group, and in particular, $R_{30}$ may be an amine group.

The ratio of the curing agent in the polymerizable composition is not particularly limited. The ratio can be adjusted so that the desired hardenability can be ensured in consideration of, for example, the ratio or type of the curable component such as the first monomer and the second monomer, and the like contained in the composition. For example, the curing agent may be contained in the polymerizable composition in an amount of about 0.02 mol to 1.5 mol, or so, per mol of the second monomer contained in the polymerizable composition or the compound and other phthalonitrile compounds. However, the above ratios are only examples of the present application. In general, if the ratio of the curing agent in the polymerizable composition increases, the process window tends to become narrow, and if the ratio of the curing agent decreases, the hardenability tends to become insufficient, so that considering these points, a suitable ratio of the curing agent can be selected.

In one example, the processing temperature, that is, the melting temperature or the glass transition temperature, of the polymerizable composition may be in a range of 100° C. to 300° C. In this case, the polymerizable composition may have a process window, that is, an absolute value of the difference (To−Tp) between the processing temperature (Tp) and a curing reaction initiation temperature (To) of the compound of Formula 1 or the like, of 50° C. or higher, 70° C. or higher, or 100° C. or higher. In the present application, the term curing reaction initiation temperature may mean a temperature at the time when polymerization or curing of the polymerizable composition or a prepolymer to be described below is started. In one example, the curing reaction initiation temperature (To) may be higher than the processing temperature. By using the polymerizable composition, such a range may be advantageous in ensuring proper workability, for example, in the course of producing a composite to be described below. Here, the upper limit of the window process is not particularly limited, but for example, the absolute value of the difference (To−Tp) between the processing temperature (Tp) and the curing reaction initiation temperature (To) may be 300° C. or lower, or 200° C. or lower.

The polymerizable composition may further comprise various additives. An example of such an additive can be exemplified by various fillers. The kind of the material that can be used as the filler is not particularly limited, and all the known fillers suitable for the intended use may be used. The exemplary filler includes a metal material, a ceramic material, glass, metal oxide, metal nitride or a carbon-based material, and the like, but is not limited thereto. In addition, the form of the filler is also not particularly limited and may be various forms, for example, a fibrous material such as aramid fiber, glass fiber, carbon fiber or ceramic fiber, or a woven fabric, nonwoven fabric, string or cord formed by the material, particles comprising nanoparticles, polygons or other amorphous forms, and the like. Here, as the carbon-based material, graphite, graphene or carbon nanotubes, and the like, or derivatives and isomers such as their oxides can be exemplified.

The present application also relates to a prepolymer formed by reaction of the polymerizable composition, that is, the polymerizable composition comprising the compound of Formula 1.

In the present application, the term prepolymer state is a state where the reaction of the first monomer and the second monomer with the curing agent in the polymerizable composition takes place to some extent (for example, a state where polymerization in a step of a so-called stage A or B has occurred), but do not reach the completely polymerized state and exhibit appropriate fluidity, and for example may mean a state capable of processing a composite, as described below.

The prepolymer may also exhibit excellent hardenability, a suitable processing temperature and a wide process window. Also, the prepolymer may exhibit stability over time even when it is stored at room temperature for a long period of time.

In one example, the processing temperature, that is, the melting temperature or the glass transition temperature, of the prepolymer may be in a range of 100° C. to 300° C. In this case, the prepolymer may have a process window, that is, an absolute value of the difference (To−Tp) between the processing temperature (Tp) and a curing reaction initiation temperature (To) of the prepolymer, of 50° C. or higher, 70° C. or higher, or 100° C. or higher. In one example, the curing reaction initiation temperature (To) may be higher than the processing temperature. By using the prepolymer, such a range may be advantageous in ensuring proper workability, for example, in the course of producing a composite to be described below. Here, the upper limit of the window process is not particularly limited, but for example, the absolute value of the difference (To−Tp) between the processing temperature (Tp) and the curing reaction initiation temperature (To) may be 300° C. or lower, or 200° C. or lower.

The prepolymer may further comprise any known additive in addition to the above components. As an example of such an additive, the above-mentioned fillers and the like can be exemplified, without being limited thereto.

The present application also relates to a composite. The composite may comprise the above-described phthalonitrile resin and filler. As described above, the present application can achieve excellent hardenability, a low melting temperature and a wide process window through the first monomer and the second monomer, and accordingly, a so-called reinforced resin composite (reinforced polymer composite) comprising various fillers can be easily formed. The composite thus formed may comprise the phthalonitrile resin and the filler, and for example, may be applied to various applications including durables, and the like for automobiles, airplanes, ships or the like.

The kind of the filler is not particularly limited and may be suitably selected in consideration of the intended use. The usable filler can be exemplified by a fibrous material such as carbon fiber, aramid fiber, glass fiber or ceramic fiber, or a woven fabric, nonwoven fabric, string or cord formed by the material, or a carbon nanomaterial such as carbon nanotube or graphene, but is not limited thereto.

Also, the ratio of the filler is not particularly limited, and may be set in an appropriate range depending on the intended use.

The method of forming the prepolymer or the like, and the method for preparing the composite by combining such a prepolymer or the like with the filler, followed by processing and curing, and the like may be carried out according to known methods.

The present application can provide a polymerizable composition, a prepolymer, a phthalonitrile resin and a composite.

EXAMPLES

Hereinafter, phthalonitrile resin and the like of the present application will be specifically described by way of examples and comparative examples, but the scope of the resins and the like is not limited to the following examples.

1. NMR (Nuclear Magnetic Resonance) Analysis

NMR analysis was carried out by using a 500 MHz NMR equipment from Agilent as the manufacturer's manual. A sample for NMR measurement was prepared by dissolving the compound in DMSO (dimethyl sulfoxide)-d6.

2. DSC (Differential Scanning Calorimetry) Analysis

DSC analysis was carried out in a $N_2$ flow atmosphere using a Q20 system from TA instrument while raising the temperature from 35° C. to 450° C. at a heating rate of 10° C./min.

3. TGA (Thermogravimetric Analysis) Analysis

TGA analysis was performed using a TGA e850 instrument from Mettler-Toledo. In the case of the compounds prepared in Preparation Examples, they were analyzed in a $N_2$ flow atmosphere while raising the temperature from 25° C. to 800° C. at a heating rate of 10° C./min.

Preparation Example 1. Synthesis of Compound (PN1)

A compound of Formula P below was synthesized in the following manner. 32.7 g of a compound of Formula Q below and 120 g of DMF (dimethylformamide) were put into a 3 neck RBF (round bottom flask) and dissolved by stirring at room temperature. Subsequently, 51.9 g of a compound of Formula R was added and 50 g of DMF was added, and then dissolved by stirring. Subsequently, 62.2 g of potassium carbonate and 50 g of DMF were added together and the temperature was raised to 85° C. with stirring. After reacting for about 5 hours in the above state, it was cooled to room temperature. The cooled reaction solution was neutralized and precipitated by pouring it into a 0.2N hydrochloric acid aqueous solution, and washed with water after filtering. The filtered reactant was then dried in a vacuum oven at 100° C. for 1 day, and after removing water and the residual solvent, a compound (PN6) of Formula L below was obtained in a yield of about 80 wt %. The

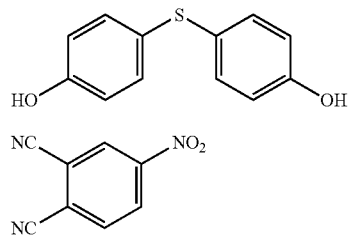

[Formula Q]

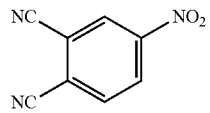

[Formula R]

Preparation Example 2. Synthesis of Compound (PN2)

Figure 2:
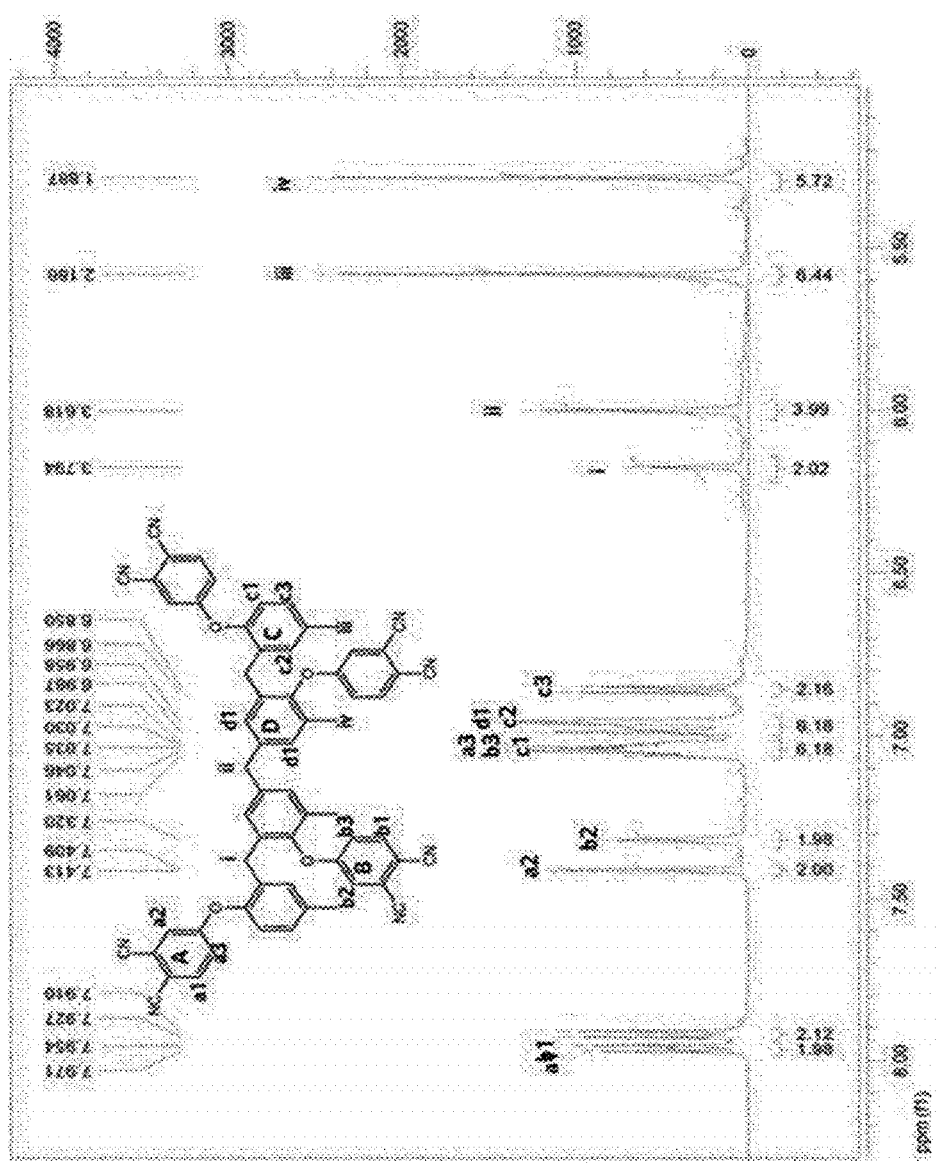

A compound of Formula S was synthesized in the following manner. 103.09 g of 4,4'-methylenebis[2-[(2-hydroxy-5-methylphenyl)methyl]-6-methyl-phenol and 152.39 g of 4-nitrophthalonitrile were introduced together with 145.95 g of potassium carbonate and 605.9 g of DMF to a 3 neck flask for reaction. As the flask for reaction, a 1000 mL volume flask equipped with a mechanical stirrer, a distillation apparatus and a nitrogen inlet was used. Subsequently, a nitrogen stream was passed through the flask for reaction, and the mixture was heated and stirred at a temperature of about 85° C. for about 5 hours. Subsequently, the mixture in the flask was cooled to room temperature (about 20° C. to 25° C.), and the mixture was precipitated in 4 L of a hydrochloric acid aqueous solution (concentration: 0.2N) and then filtered to remove residual inorganic salts and DMF. The powder obtained after filtration was dispersed again in methanol (1 L) and filtered again to remove organic substances, and the reactant was vacuum-dried in an oven at 50° C. to obtain a target product. The results of the NMR analysis carried out on the target product were attached to FIG. 2.

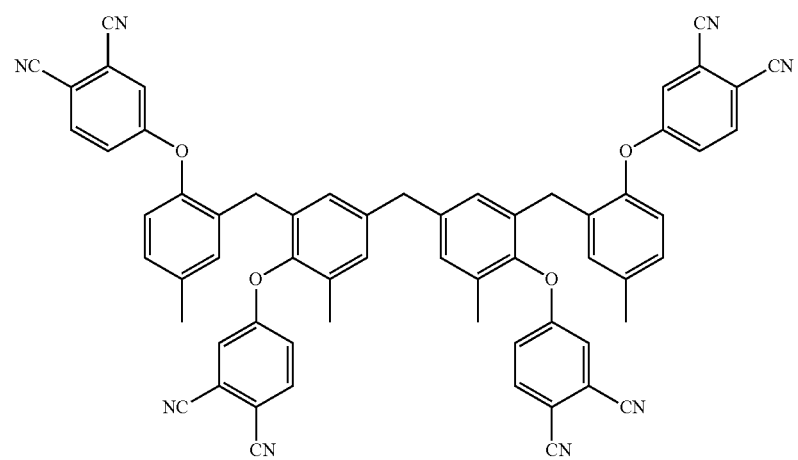

[Formula S]

NMR results for the compound of Formula P above were described in FIG. 1.

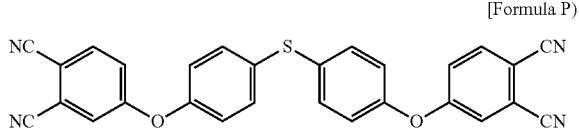

[Formula P]

Preparation Example 3. Synthesis of Curing Agent (CA)

Figure 3:
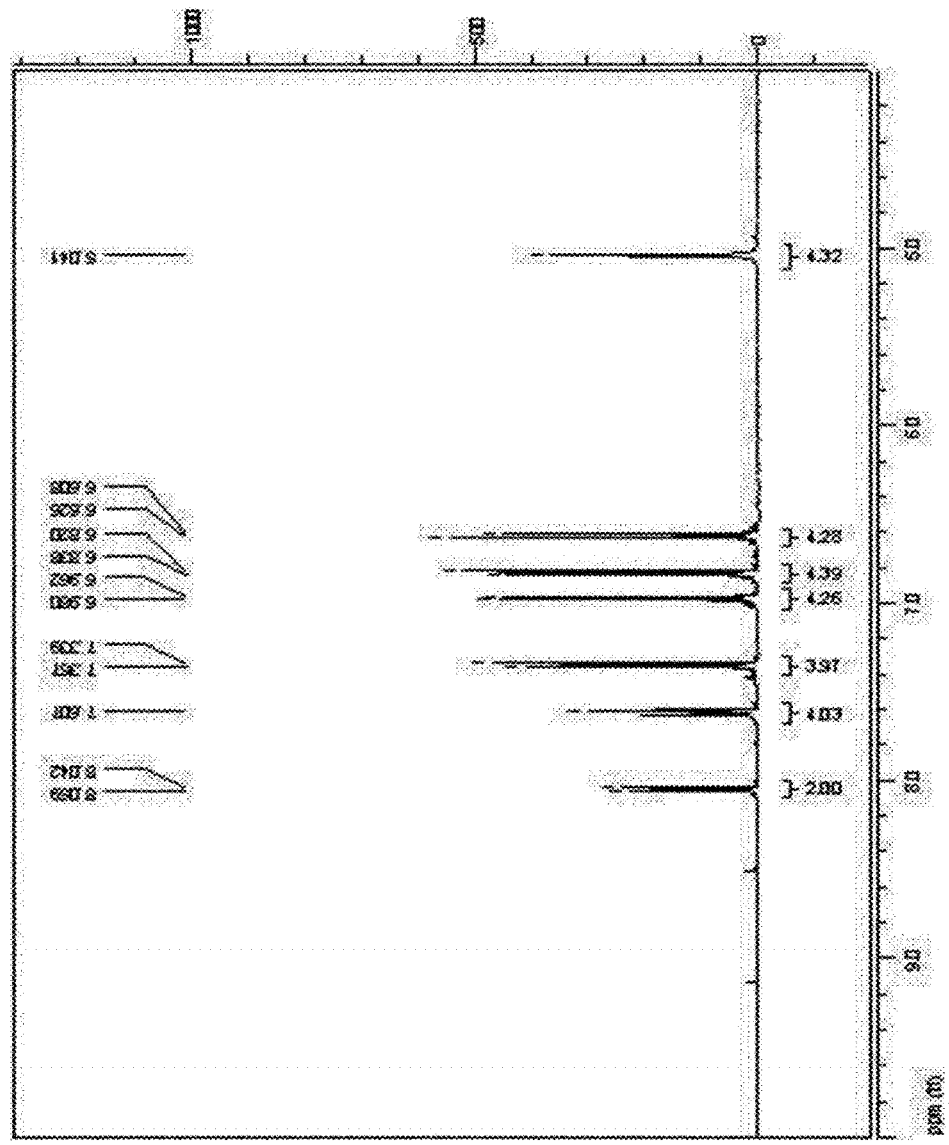

A compound of Formula T below was synthesized in the following manner. In a 100 mL volume round flask connected with a nitrogen line and a mechanical stirrer, 88.11 g of 4,4'-oxybisbenzenamine and 34.12 g of 4,4'-oxydi (phthalic anhydride) were stirred together with 500 ml of N-methyl-2-pyrrolidone. When the powder was completely dissolved, 115.4 g of toluene was further added, and then a Dean-Stark trap was installed. Toluene was also charged in the Den-Stark trap to maintain a constant amount of toluene. Then, 11.5 ml of pyridine and 6.8 ml of γ-valerolactone were added in turn using a syringe, and then the mixture was stirred at 175° C. for 3 hours. After removing the toluene and water from the Dean-Stark trap, the toluene present in the flask was completely removed by further heating it for about 2 hours. After completion of the reaction, the solution was cooled to room temperature was slowly dropped and precipitated in 3 L of methanol in order to remove 4,4'-diaminodiphenylether (ODA) and N-methyl-2-pyrrolidone (NMP), and then filtered to obtain a powder comprising a target product. The results of NMR (nuclear magnetic resonance) analysis carried out on the target product were attached to FIG. 3.

TABLE 1

|  | Molar ratio of PN2 (mol %) | Weight ratio of PN2 (wt %) | Heat distortion temperature (HDT, ASTM D648) | Residue at 800° C. (%) |
|---|---|---|---|---|
| Example 1 | 5 | 9.9 | 257° C. | 69.9 |
| Example 2 | 25 | 40.8 | 310° C. | 74.7 |
| Example 3 | 50 | 67.4 | 342° C. | 74.9 |
| Comparative Example | 0 | 0 | 240° C. | 67.7 |

[Formula T]

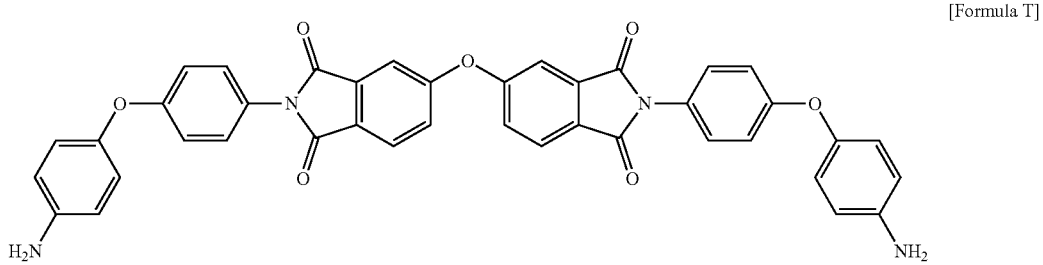 [SMILES: Nc1ccc(Oc2ccc(N3C(=O)c4ccc(Oc5ccc6c(c5)C(=O)N(c5ccc(Oc7ccc(N)cc7)cc5)C6=O)cc4C3=O)cc2)cc1]

Example 1

To the mixture in which the compound (PN1) of Preparation Example 1 and the compound (PN2) of Preparation Example 2 were mixed so that the molar ratio of PN1:PN2 was 95:5 (weight ratio 1:0.11), the curing agent (CA) of Preparation Example 3 was formulated so as to be present at 0.18 mol per mol of the mixture, to prepare a polymerizable composition, and the physical properties were evaluated.

Example 2

To the mixture in which the compound (PN1) of Preparation Example 1 and the compound (PN2) of Preparation Example 2 were mixed so that the molar ratio of PN1:PN2 was 3:1 (weight ratio 1:0.69), the curing agent (CA) of Preparation Example 3 was formulated so as to be present at 0.18 mol per mol of the mixture, to prepare a polymerizable composition, and the physical properties were evaluated.

Example 3

To the mixture in which the compound (PN1) of Preparation Example 1 and the compound (PN2) of Preparation Example 2 were mixed so that the molar ratio of PN1:PN2 was 1:1 (weight ratio 1:2.07), the curing agent (CA) of Preparation Example 3 was formulated so as to be present at 0.18 mol per mol of the mixture, to prepare a polymerizable composition, and the physical properties were evaluated.

Comparative Example 1

A polymerizable composition was prepared by formulating the curing agent (CA) of Preparation Example 3 to the compound (PN1) of Preparation Example 1 so as to be present at about 0.18 mol per mol of the compound (PN1), and the physical properties were evaluated.

The results of analyzing the compositions of the Examples and Comparative Examples are described in Table 1 below.

The invention claimed is:

1. A polymerizable composition comprising a first monomer containing two functional groups derived from phthalonitrile and a second monomer containing three or more functional groups derived from phthalonitrile,
wherein the first monomer is a compound of Formula 1 below:

Formula 1

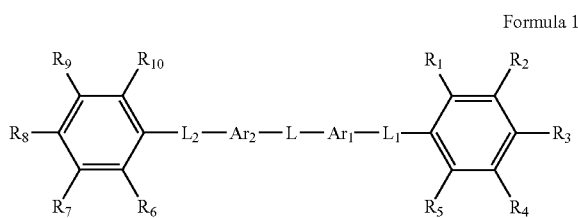

wherein, $Ar_1$ and $Ar_2$ are each independently an aromatic divalent radical, L, $L_1$ and $L_2$ are each independently a single bond, an alkylene group, an alkylidene group, an oxygen atom or a sulfur atom, and $R_1$ to $R_{10}$ are each independently hydrogen, an alkyl group, an alkoxy group, an aryl group or a cyano group, provided that at least two of $R_1$ to $R_5$ are each a cyano group and at least two of $R_6$ to $R_{10}$ are each a cyano group, and
wherein the second monomer is a compound of Formula 3, $$Ar_3\text{-}L_3\text{-}Ar_4\text{-}L_4\text{-}Ar_5\text{-}L_5\text{-}Ar_6 \qquad \text{Formula 3:}$$

wherein, $Ar_3$ and $Ar_6$ are the same or different aryl groups from each other, $Ar_4$ and $Ar_5$ are the same or different arylene groups from each other, $L_3$ to $L_5$ are each independently an alkylene group, an alkylidene group, an alkenylene group or an alkynylene group, where $Ar_3$ to $Ar_6$ are each substituted with at least one substituent represented by Formula 4,

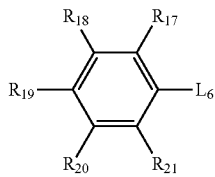

Formula 4 wherein, $L_6$ is an alkylene group, an alkylidene group, an oxygen atom or a sulfur atom, and $R_{17}$ to $R_{21}$ are each independently hydrogen, an alkyl group, an alkoxy group, an aryl group or a cyano group, provided that at least two of $R_{17}$ to $R_{21}$ are each a cyano group.

2. The polymerizable composition according to claim 1, wherein the aromatic divalent radical in Formula 1 is a divalent radical derived from an aromatic compound represented by Formula 2 below:

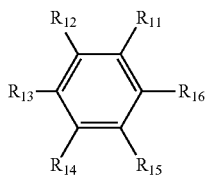

Formula 2 wherein, $R_{11}$ to $R_{16}$ are each independently hydrogen, an alkyl group, an alkoxy group or an aryl group, provided that at least two of $R_{11}$ to $R_{16}$ each form a radical.

3. The polymerizable composition according to claim 2, wherein $R_{11}$ and $R_{14}$ in Formula 2 each form a radical.

4. The polymerizable composition according to claim 1, wherein $L_1$ and $L_2$ are each an oxygen atom and L is a sulfur atom.

5. The polymerizable composition according to claim 1, wherein $L_3$ to $L_5$ are each independently an alkylene group or alkylidene group having 1 to 4 carbon atoms.

6. The polymerizable composition according to claim 1, wherein $Ar_3$ to $Ar_6$ are each substituted with at least one alkyl group.

7. The polymerizable composition of claim 1, wherein $Ar_4$ and $Ar_5$ are each a phenylene group.

8. The polymerizable composition according to claim 7, wherein in $Ar_4$, $L_3$ is bonded to a meta position based on the position where $Ar_4$ is bonded to L4, and in $Ar_5$, $L_5$ is bonded to a meta position bade on the position where $Ar_5$ is bonded to $L_4$.

9. The polymerizable composition according to claim 7, wherein in $Ar_4$, the substituent of Formula 4 is substituted at a meta or para position based on the position where $Ar_4$ is bonded to $L_4$, and in $Ar_5$, the substituent of Formula 4 is substituted at a meta or para position based on the position where $Ar_5$ is bonded to $L_4$.

10. The polymerizable composition according to claim 7, wherein in $Ar_4$, the alkyl group having 1 to 4 carbon atoms is substituted at a meta or para position based on the position where $Ar_4$ is bonded to $L_4$, and in $Ar_5$, the alkyl group having 1 to 4 carbon atoms is substituted at a meta or para position based on the position where $Ar_5$ is bonded to $L_4$.

11. The polymerizable composition according to claim 1, wherein $Ar_3$ and $Ar_6$ are each a phenyl group.

12. The polymerizable composition according to claim 11, wherein in $Ar_3$, the substituent of Formula 3 is substituted at an otho or meta position based on the position where $Ar_3$ is bonded to $L_3$, and in $Ar_6$, the substituent of Formula 3 is substituted at an otho or meta position based on the position where $Ar_6$ is bonded to $L_5$.

13. The polymerizable composition according to claim 11, wherein in $Ar_3$, the alkyl group having 1 to 4 carbon atoms is substituted at an otho or meta position based on the position where $Ar_3$ is bonded to $L_3$, and in $Ar_6$, the alkyl group having 1 to 4 carbon atoms is substituted at an otho or meta position based on the position where $Ar_6$ is bonded to $L_5$.

14. The polymerizable composition according to claim 1, comprising 5 to 250 parts by weight of the second monomer relative to 100 parts by weight of the first monomer.

15. The polymerizable composition according to claim 1, wherein a melting temperature ($T_m$) of a homopolymer of the second monomer is higher than a melting temperature ($T_m$) of a homopolymer of the first monomer.

* * * * *